United States Patent
Chancey et al.

(10) Patent No.: US 11,385,210 B2
(45) Date of Patent: Jul. 12, 2022

(54) APPARATUS AND METHODS FOR PROVIDING CORRECTED READINGS IN ODOR INTENSITY LEVEL MONITORING INSTRUMENTATION AND CONCURRENT ODOR INTENSITY AND ODORANT CONCENTRATION MEASUREMENTS

(71) Applicant: HEATH CONSULTANTS, INC., Houston, TX (US)

(72) Inventors: Steven Chancey, Houston, TX (US); Paul Wehnert, Houston, TX (US)

(73) Assignee: HEATH CONSULTANTS, INC., Houston, TX (US)

( * ) Notice: Subject to any disclaimer, the term of this patent is extended or adjusted under 35 U.S.C. 154(b) by 0 days.

(21) Appl. No.: 17/585,040

(22) Filed: Jan. 26, 2022

(65) Prior Publication Data
US 2022/0146478 A1    May 12, 2022

Related U.S. Application Data

(62) Division of application No. 14/856,203, filed on Sep. 16, 2015, now Pat. No. 11,243,196.
(Continued)

(51) Int. Cl.
G01N 33/00 (2006.01)

(52) U.S. Cl.
CPC ..... *G01N 33/0001* (2013.01); *G01N 33/0006* (2013.01)

(58) Field of Classification Search
CPC .............. G01N 33/0001; G01N 33/0006
See application file for complete search history.

(56) References Cited

U.S. PATENT DOCUMENTS 3,686,930 A * 8/1972 Kniebes ............. G01N 33/0044
73/23.35
5,060,505 A   10/1991 Tury et al.
(Continued)

OTHER PUBLICATIONS

Bacharach, Inc., Odorometer Portable Gas Odorant Tester; Part No. 5110-0200; Operation and Maintenance Manual, Instruction P/N 0023-9125; Rev. 17—Jun. 2011.
(Continued)

*Primary Examiner* — Lisa M Caputo
*Assistant Examiner* — Alex T Devito
(74) *Attorney, Agent, or Firm* — Bracewell LLP; Douglas W. Rommelmann

(57) ABSTRACT

A system and method for concurrently measuring odorant concentration and also compensating for changes in relative air density when measuring odor intensity levels may be used to provide more accurate and reliable readings from an odorometer. Odorometers typically measure the concentration of a given target gas in a gas-air mixture. Because changes in air density make it difficult to accurately determine how much air is in the gas-air mixture sample, a method of compensating for changes in the air density is able to produce a more accurate concentration reading. By measuring the relative temperature and pressure of the air at calibration and when a particular reading is taken, the final reading can be corrected to account for changes in the air density. By correlating the odor intensity readings with odorant concentration readings a wide array of advantages may be realized.

21 Claims, 4 Drawing Sheets

Related U.S. Application Data

(60) Provisional application No. 62/218,929, filed on Sep. 15, 2015, provisional application No. 62/050,851, filed on Sep. 16, 2014.

(56) References Cited

U.S. PATENT DOCUMENTS

| | | |
|---|---|---|
| 5,844,124 A | 12/1998 | Shimokawatoko et al. |
| 5,996,396 A | 12/1999 | Marshall et al. |
| 6,196,051 B1 | 3/2001 | Marshall et al. |
| 2004/0117117 A1 | 6/2004 | Sohl, III et al. |
| 2006/0047455 A1 | 3/2006 | Catelani et al. |

OTHER PUBLICATIONS

Heath Consultants Incorporated, Odorator User's Manual Natural Gas (Methane), 2013.

Measuring Odorants in Natural Gas Pipelines; Applied Analytics Application Note No. AN-011; Applied Analytics Group BV; Revised Oct. 18, 2013, 6 pages.

Montemarano, R.; Determining Proper Odorant Level; Heath Consultants, Inc., Oct. 2014; 4 pages.

Odorization Manual; Operating Section Report; Laboratory and Chemical Service Committee; American Gas Association; 1983; 58 pages.

Odorization Manual; Operating Section; Transmission Measurement Committee and Former Chemical and Analytical Services Task Committee; American Gas Association; Revised Dec. 2000, 62 pages.

Sasse, F. and Flynn, E., Measuring Odorant Levels in the Pipeline with Reliable Analytical Instruments; Natural Gas Odorization Conference & Exhibition; May 1-2, 2013; pp. 1-30; Houston, TX.

Sasse, F., and Flynn, E., Measuring Odorant Levels in the Pipeline with Reliable Analytical Instruments; 2010 Natural Gas Odorization Conference; May 25-26, 2010; 17 pages, Houston, TX.

Wehnert, P. D., Proper Testing of Odorant Concentration Levels; American School of Gas Measurement Technology, 2002 Proceedings; pp. 294-297.

Yando, D., Proper Testing of Odorant Levels in Natural Gas, IURC Pipeline Safety Seminar; Jul. 14, 2010; 22 pages.

\* cited by examiner

APPARATUS AND METHODS FOR PROVIDING CORRECTED READINGS IN ODOR INTENSITY LEVEL MONITORING INSTRUMENTATION AND CONCURRENT ODOR INTENSITY AND ODORANT CONCENTRATION MEASUREMENTS

CROSS-REFERENCE TO RELATED APPLICATIONS

This application is a divisional of U.S. application Ser. No. 14/856,203, filed Sep. 16, 2015, which claims priority under 35 USC 119(e) to U.S. Provisional Application No. 62/050,851 filed Sep. 16, 2014, and U.S. Provisional Application No. 62/218,929 filed Sep. 15, 2015, both of which are incorporated herein by reference in their entirety.

FIELD

The present invention relates to apparatus and methods for detecting combustible gas odor intensity levels and providing concurrent measurements of odor intensity and odorant concentration in a gas stream.

BACKGROUND

Combustible gases are commonly odorized to provide a simple, effective, and safe way for an individual to detect the presence of a combustible gas. An odorant is frequently deployed into the combustible gas stream. This odorization allows potential gas leaks and other dangerous conditions to be detected by an individual with an average sense of smell. Detection of the odor does not require the use of any particular tools or equipment, but equipment may be used to detect the odor. It is to be appreciated that references to "gas" or "target gas" in a gas-air mixture implies odorized gas which is not 100% composed of any particular gas (e.g., methane or propane).

Multiple separate regulatory schemes are commonly used for regulating combustible gases world-wide. The relative concentration of a target gas in gas-air mixtures which produces a readily detectable odor intensity to a human with an average sense of smell is a commonly used factor for regulatory compliance in the United States. This system relies on human operators to gradually increase the relative concentration of a target gas in a gas-air mixture until the gas odor is readily detectable by the operator. The operator may then use a device to measure the gas concentration in that gas-air mixture. Alternate regulatory schemes may involve direct measurement of the odorant concentration in the combustible gas stream, frequently using an electro-chemical sensor. It is to be appreciated that the concentration of odorant in a target gas stream is a completely separate measurement from the concentration of a target gas in a gas-air mixture.

In order to accurately determine the concentration of gas in a gas-air mixture, the quantities of both gas and air entering a testing apparatus must be accurately known. Traditionally, a mass flow sensor has been used to accurately quantify the amount of gas entering the apparatus while air enters the apparatus via a blower or fan. Mass flow sensors are less affected by changes in elevation, weather, and/or time of year as compared to volumetric flow sensors. Many complicating factors can change the pressure and temperature of the ambient air and thus its density. This makes accurately determining the precise amount of air that has been mixed with a gas more difficult. What is needed is an alternate solution for compensating for changes in air density, such that instruments sensitive to such changes may provide accurate readings despite changing atmospheric conditions.

Due to the potential danger associated with combustible gases, many areas have developed regulatory schemes governing the odorants frequently added to combustible gases. Stand-alone odor intensity meters or odorometers, may be used to determine the relative concentration of gas in a gas-air mixture at which a human operator determines there is a readily detectable odor. Odorant concentration devices may alternatively be used to determine the actual concentration of an odorant as opposed to the human perceived intensity of the odor. Each of these techniques has benefits and limitations. In order to provide high quality of odor intensity and odorant concentration data, what is needed is a device which allows for the concurrent measurement of odor intensity and odorant concentration from substantially the same sample.

SUMMARY

In one aspect, embodiments disclosed relate to a method for compensating and/or correcting odorometer device readings for changes in relative air density. Odorometers may be used to measure the concentration of a given target gas in a gas-air mixture. Changes in the air density may make it difficult to accurately quantify the amount of air in the gas-air mixture. By applying a correction technique that accounts for the changes in temperature and pressure between the conditions at which the device is calibrated and the conditions under which a given measurement is taken, a more accurate reading may be produced.

In another aspect, embodiments disclosed relate to a method for providing a corrected reading in an odorometer with a fixed speed blower.

In yet another aspect, embodiments disclosed relate to a system for measuring relative gas concentration in a sample and correcting for changes in air density. The system may comprise a metering valve, an exhaust port, a mass flow sensor, a pressure sensor, a temperature sensor, an electronics package, and a processor capable of applying a correction program to readings provided by the sensors.

In still another aspect, embodiments disclosed may relate to concurrently measuring odorant concentration in a target gas and the concentration of a target gas at a readily detectable odor intensity in a gas-air mixture. This and other embodiments may additionally record all data for analysis, training, oversight, and/or regulatory compliance.

In another aspect, embodiments disclosed relate to recording, transmitting, and/or displaying a corrected concentration of target gas in a gas-air mixture and a concurrently measured odorant concentration within the target gas.

DETAILED DESCRIPTION

Figure 1:
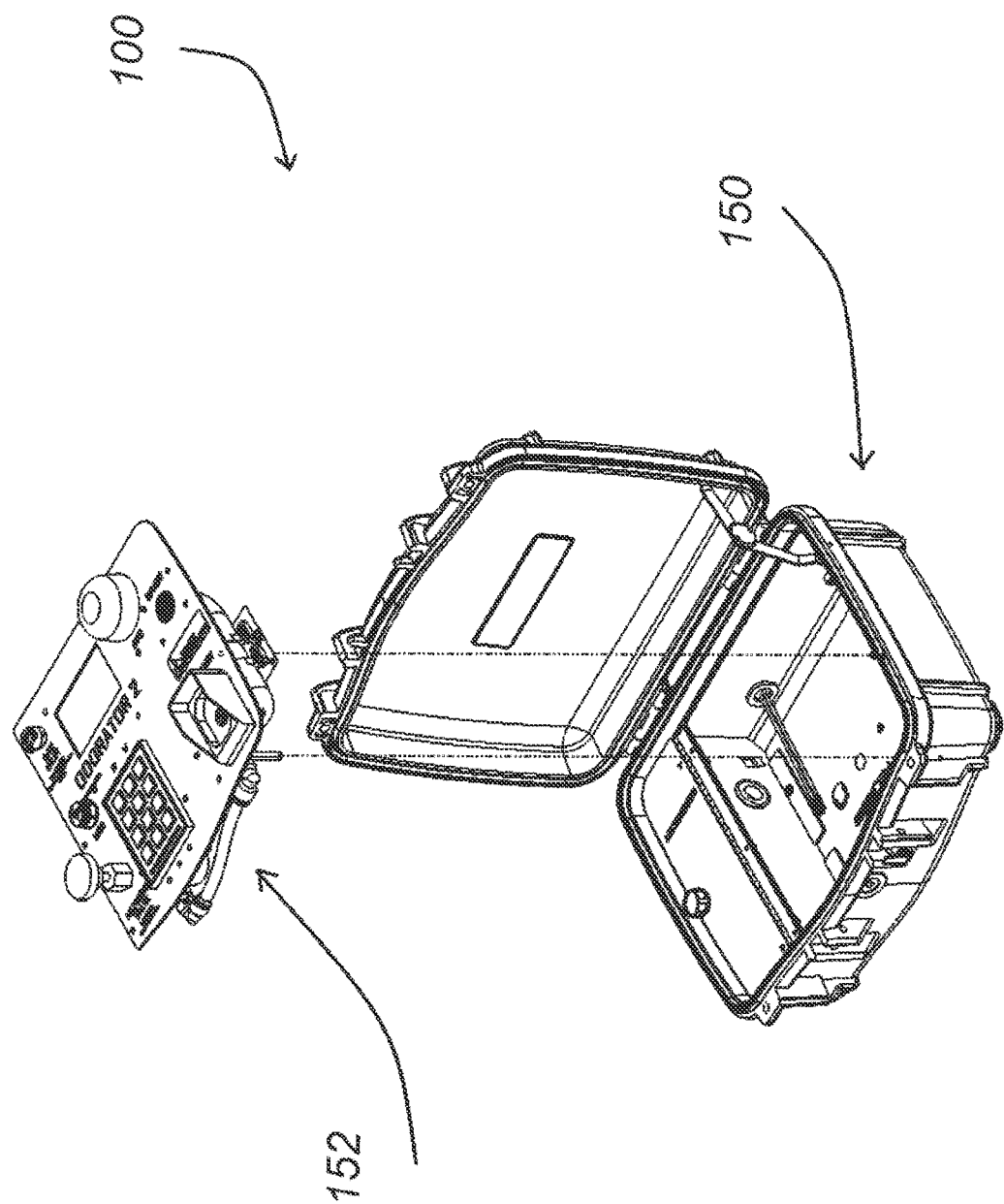
FIG. 1 depicts one potential embodiment of the top panel assembly and housing.
Figure 2:
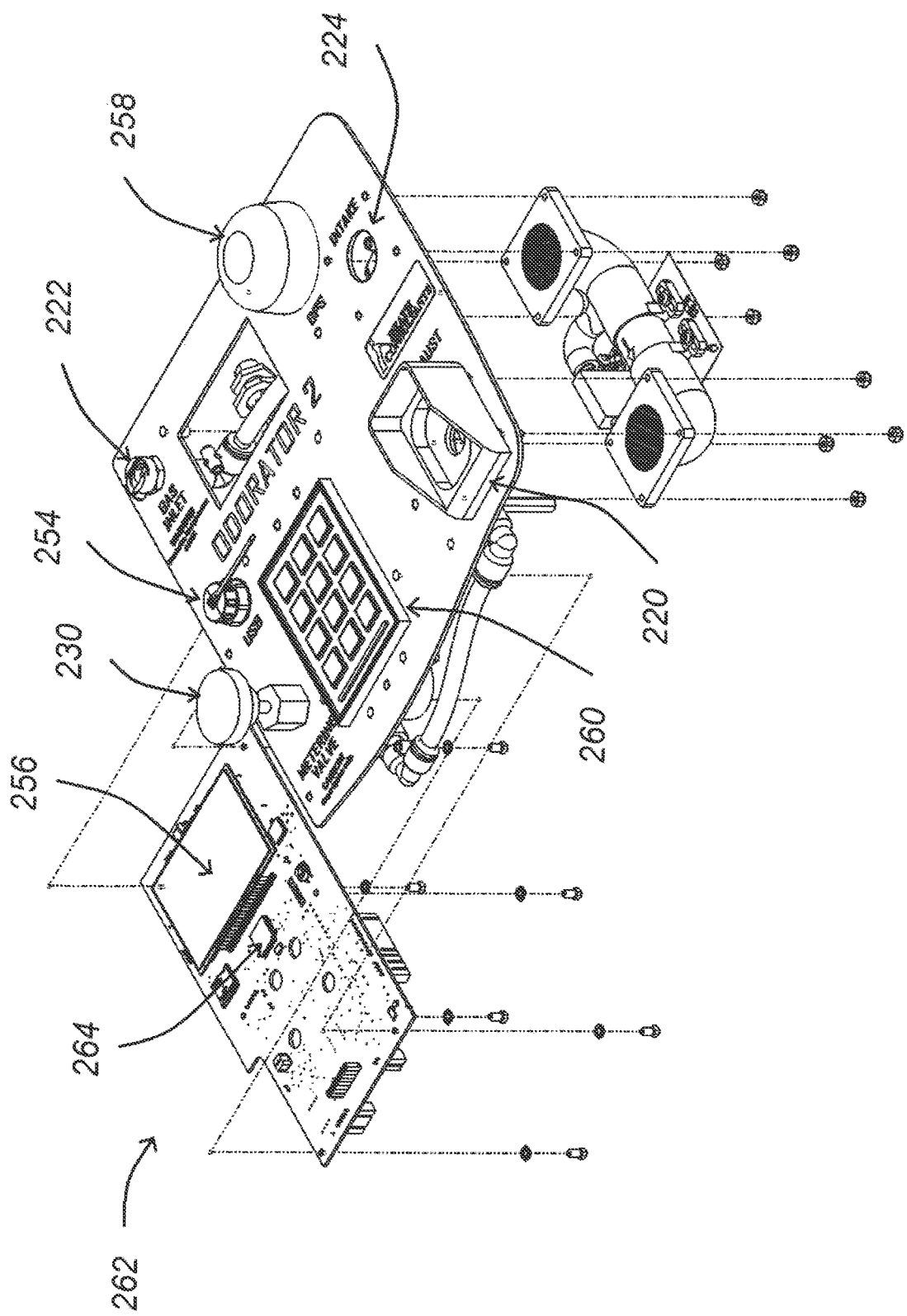
FIG. 2 illustrates a more detailed view of one embodiment of the apparatus.
Figure 3:
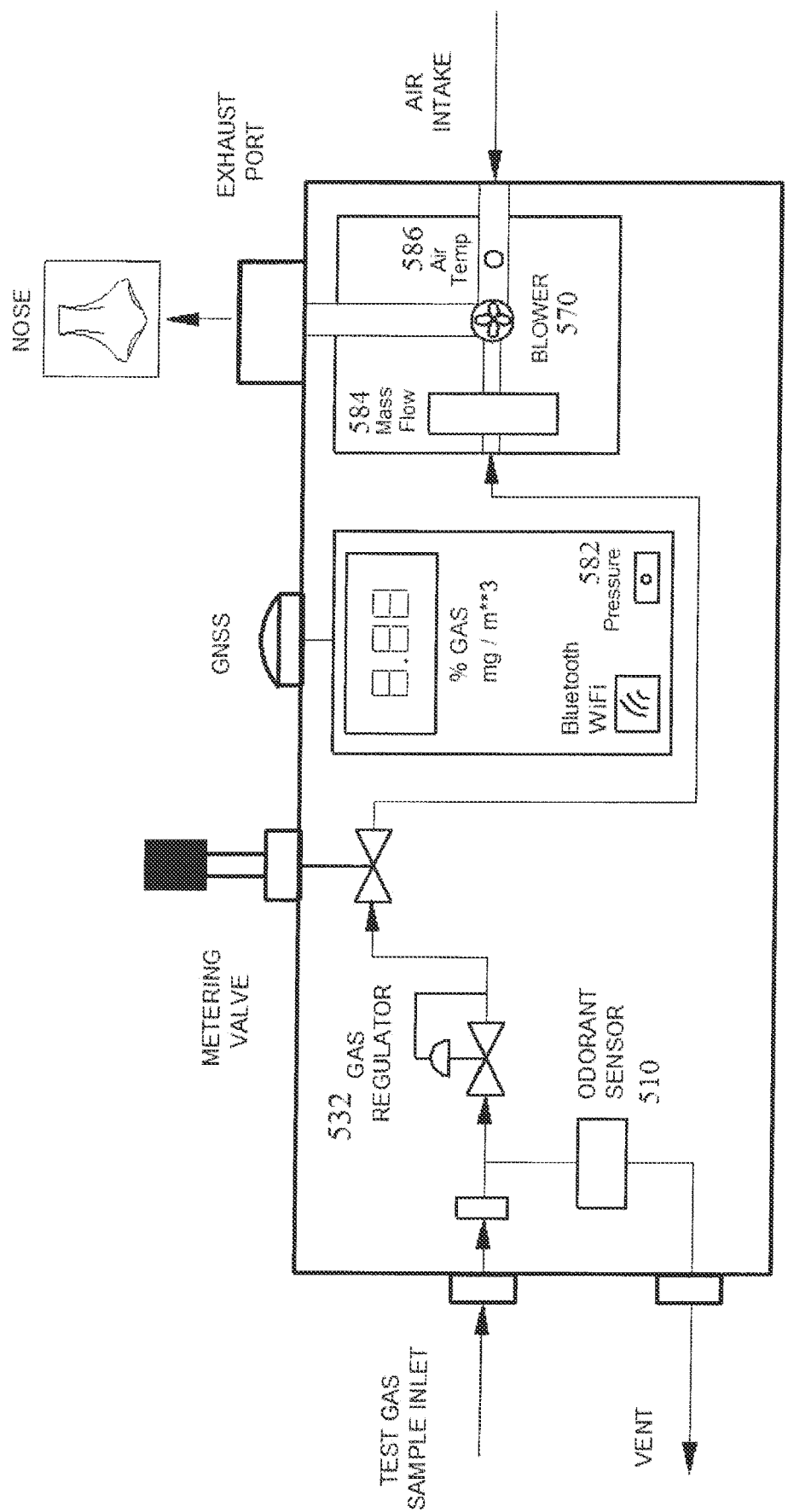
FIG. 3 depicts a block diagram of a particular disclosed embodiment.

An apparatus and method for automatically correcting odorometer readings in an apparatus used to monitor odor intensity levels in gas streams is disclosed. In a preferred embodiment, the apparatus 100 may concurrently measure the concentration of an odorant in a gas stream and measure the odor intensity level from that same gas stream sample. In some embodiments, the apparatus 100 may contain a top panel assembly 152 and a housing 150. Components may also include a flow metering valve 230 to introduce gas samples to the apparatus 100 through gas inlet 222, a sample gas regulator 532, a solid state mass flow sensor 584, an absolute pressure sensor 582, a flow system temperature sensor 586, an air intake 224, a blower 570 to mix the gas sample with air for evaluation, electronics 262 with non-volatile memory storage, a processor 264, an odorant concentration sensor 510, a GNSS receiver 258, communications 254 which may include USB, Bluetooth, and/or WiFi, a digital display 256, and/or a keypad 260. The apparatus 100 may produce a mix of natural gas (e.g., methane), propane gas or other combustible target gas and air in concentrations from zero to approximately 2% for natural gas or approximately 1% for propane. The operator may slowly open the flow metering valve 230 which may allow a sample gas to enter the apparatus 100 and then the operator may sniff the mixed exhaust gases at the exhaust port 220. This operation may be continued until the odor intensity level in the exhaust is readily detectable at which time the operator may press the "read" key to observe the relative percent gas concentration in air on the display 256 (e.g., digital display) and trigger the automatic recording of the dataset. In certain embodiments, the "read" key may also activate the odorant concentration sensor, causing an odorant concentration reading to be taken at substantially the same time as the odor intensity level is determined.

Atmospheric conditions may differ significantly depending on geographic location, elevation, weather conditions and/or time of year, thus affecting the volumetric flow of a substantially fixed speed blower 570 due to potential changes in air density. As such, an instrument sensitive to changes in air density may beneficially provide a method to compensate for changes in air density and correct its readings accordingly.

In one embodiment, the apparatus 100 corrects all readings using a combination of local meteorology sensors and an embedded program in the firmware. For example, pressure, temperature, and optionally humidity sensors, among others, may be used. Blower speed may be held constant. Reading correction may be based on the ratio of calibration air density to the actual air density measured while performing a test. Sample gas influence may be ignored if desired, as it usually contributes less than 1% error in most cases. A similar reading correction may be implemented by applying independent pressure, temperature, and optionally humidity and other sensor coefficients to air density. The difference between using independent sensor based coefficients and air density ratio is that the air density ratio typically models the correction relationship more intrinsically and because of that, it may be easier to implement in firmware.

In preferred embodiments, reading corrections based on air density ratio are derived as follows:

$$\text{Corrected Reading} = \{\text{Uncorrected Reading}\} \times k_{LCD} \times \left(\frac{\rho_{cal}}{\rho_{actual}}\right) \quad \text{Equation 1}$$

where,
The "uncorrected reading" may be obtained by digitizing and applying the output of the mass flow sensor 584 to a memory-based mass flow sensor response curve for a given calibration target value and type (e.g., 1.00% methane);

$k_{LCD}$ is a scale factor to normalize the reading to the calibration target value based on a reference gas and flow;

$\rho$ is air density;

$\rho_{cal}$ is the air density present at calibration;

$\rho_{actual}$ is the actual air density present while taking a reading;

To derive $\rho$:

$$PV = nRT \text{(ideal gas law)}$$

$$\rho = \frac{\text{weight}}{\text{volume}} = \frac{n}{V}$$

Therefore, $$\rho = \frac{P}{RT}\left(\text{in units of } \frac{\text{kg}}{\text{m}^3}\right)$$

Substituting $\rho$ into Equation 1 yields Equation 2 (R cancels resulting in a relative air density ratio term):

$$\text{Corrected Reading} = \qquad \text{Equation 2}$$
$$\{\text{uncorrected reading}\} \times k_{LCD} \times \left[\frac{P_{cal} \times T_{actual}}{T_{cal} \times P_{actual}}\right]$$

For algorithm deployment, let:

$$k_{cal} = \frac{P_{cal}}{T_{cal}}$$

Therefore the final algorithm is:

$$\text{Corrected Reading} = \qquad \text{Equation 3}$$
$$\{\text{uncorrected reading}\} \times k_{LCD} \times k_{cal} \times \left(\frac{T_{actual}}{P_{actual}}\right)$$

where pressure is measured in Pascals and temperature is measured in degrees Kelvin.

Figure 4:
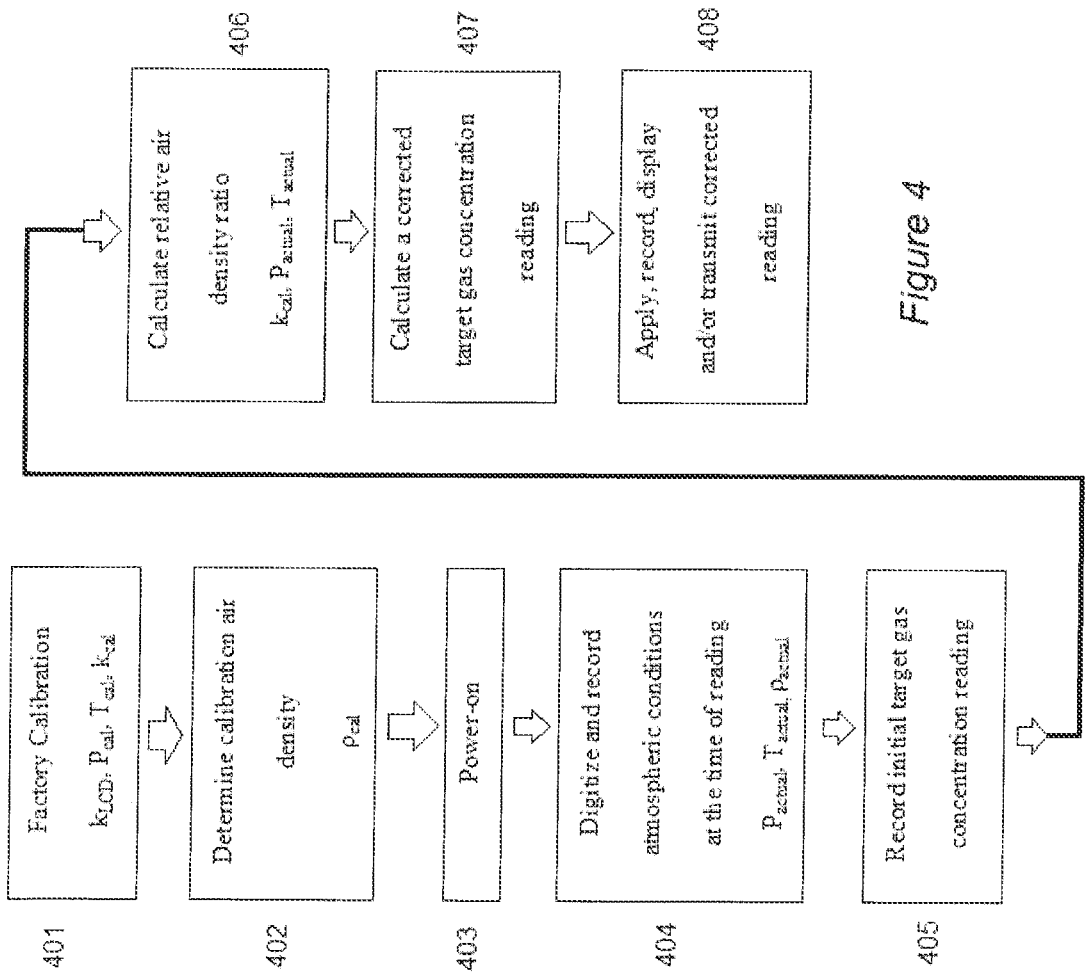
FIG. 4 illustrates a flow chart of the steps for operating certain embodiments of the disclosed apparatus.

With reference to FIG. 4, one potential method of operating and taking corrected readings using the apparatus is described below. A factory calibration 401 may be initially performed on the apparatus and the values $k_{LCD}$, $P_{cal}$, $T_{cal}$ and $k_{cal}$ may be determined and/or recorded. These values may be used to determine a calibration air density 402. Upon powering "on" the apparatus, sensors may begin continually monitoring atmospheric conditions 403. The signals from these sensors may be digitized and recorded. This monitoring may be in real-time, periodically, or when desired. Sensor data may be recorded to memory continually, periodically, and/or when desired. Sensor data averaging may optionally be employed to filter out unwanted noise. When the time comes to take a target gas concentration reading, the sensors may be measured and/or digitized using the then-current actual atmospheric conditions 404 (e.g., $T_{actual}$ and $P_{actual}$). An initial reading of the target gas concentration may be taken 405. The sensor values may be used to determine the air density at which the initial reading is taken. Using the calibration and actual atmospheric conditions, the relative air density ratio may be calculated using the Equation 3 or a similar equation 406. This ratio may be applied to correct the initial target gas concentration reading 407. A corrected reading, which may be a corrected relative percent gas concentration in a gas-air mixture, may be displayed to the operator and/or the dataset may be recorded and/or transmitted 408.

In addition to correcting odor intensity readings based on changes in atmospheric conditions, certain embodiments may also be equipped with odorant concentration sensors. It is to be appreciated that odor intensity is commonly perceived by a human as described above, while odorant concentration is typically a quantized reading measured by a device. Generally, stand-alone odorant concentration measurement instruments are known in the art.

When measuring the concentration of an odorant, the result may be a quantized concentration, which may be expressed in $mg/m^3$, parts-per-million (ppm) or any other appropriate unit. Measuring the concentration of odorants, both naturally occurring and artificially added, may be performed through many analytical methods. Odorants commonly used in combustible gas streams include mercaptans, thiophenes, sulfur containing molecules and/or others. Various electro-chemical sensors may be employed. Additionally, the concentration of odorants in gas systems may be measured using spectrophotometry, UV spectroscopy, ion-mobility spectrometry, flame ionization, gas chromatography, specific gravity, mass spectrometry, infrared sensing and/or other techniques.

Using certain embodiments of the disclosed device, concurrent odor intensity and odorant concentration measurements may be obtained. Additionally, these concurrent measurements may be obtained by two independent sensor channels. This arrangement may allow for rapid data acquisition as well as fully correlated data for further corroboration and analysis. While stand-alone instruments may perform similar individual measurements, concurrent analysis provides for a wider range of advantages over measurement of either odor intensity or odorant concentration in isolation. By measuring both variables concurrently, using substantially the same gas samples, the measurements are inherently coordinated. This coordination may be used to cross check each measurement against the other and ensure a high degree of accuracy. These measurements may be compared with previous measurements and used to identify anomalous measurements which may indicate a faulty reading. If the measured odor intensity does not generally align with the measured odorant concentration, it is likely a sign of a problem in at least one of the measurement systems, possibly including the human operator. The measuring device may be damaged and may be producing inaccurate readings. Alternatively, the human operator may be more or less sensitive during a particular measurement as compared to previous measurements. This redundant and correlated data allows for greater confidence that a particular measurement is correct.

Measuring both of these factors concurrently allows for more educated deployment of odorant into the gas stream and may help troubleshoot problems associated with odorant deployment. Analysis of this correlated data may help ensure that odorant is deployed sufficiently and/or efficiently depending on the circumstances. Additional benefits include increased regulatory compliance across a wide range of standards, more objective measurement as compared to relying exclusively on the sensitivity of a single human operator, the ability to cross check multiple human operators against each other and many others. By taking concurrent measurements, significant man hours and the resources associated with line testing may be saved. This may result in an overall reduction in the cost of odor related testing for combustible gas related industries.

Many embodiments of the disclosed apparatus 100 may optionally be configured to automatically record all readings, a dataset, geographic locations, UTC timestamps, and/or waypoints. The apparatus 100 may additionally include Global Navigation Satellite System ("GNSS") 258 receivers using the GPS, GLONASS, Galileo, Beidou and/or other GNSS systems. Automatic timestamp and real-time clock management may be provided via the GNSS. Additionally, the apparatus 100 may include an odorization survey audit system for regulatory compliance. The apparatus 100 may be operated in conjunction with PC software for database management, mapping, report generation, tools and/or ease of integration with corporate GIS and/or asset management systems. The apparatus 100 may be connected to other systems via USB, Bluetooth and/or WiFi communications 254. By automatically recording the timestamp, geographical location, odor intensity, and/or odorant concentration data the correlation between the two primary sensors channels may be preserved for analysis.

Certain embodiments of the apparatus 100 may be configured to take advantage of the recording and communication abilities for operator qualification, training, and/or monitoring reasons. Using the automatic data recording and communication capabilities, a remotely located trainer may observe the operations of the device in real-time or near-real-time. The trainer may also review recorded data at a later time. A trainer or supervisor may perform any and/or all of these activities using the WiFi or other connectivity found in certain embodiments of the apparatus. This connectivity may be supported using a web based or other type of computer application. Data to be monitored or reviewed includes, but is not limited to, odor intensity readings, odor concentration readings, GNSS location readings, timestamps, and waypoints. Software tools for report generation may include maps and excel compatible files. These tools may document the operator's experience, qualification and/or training among other possible variables. Work schedule and/or productivity of the operator may additionally be monitored. By verifying the geographic location and timestamps correlated with the data recorded, the general schedule and productivity of the operator may be extrapolated. This data may be used in order to promote operational efficiency and verify actual reading locations.

A flow self-test of the apparatus may be performed by an operator to check that the apparatus 100 is working properly. The flow self-test typically requires a source of gas (e.g., pipeline gas or propane from a tank). First, the operator may purge the apparatus 100 with gas, condition the apparatus (in part by allowing the apparatus to reach approximately the same temperature as the gas), and then zero the apparatus.

The operator may verify the metering valve 230 is fully or at least significantly opened. The operator may wait for the system to adjust, typically at least 10 seconds, and then press a "Self-Test" key. The uncorrected reading on the display 256 should be greater than or equal to the calibration target value (e.g., 1.00%). The calibration target value is the percent concentration of gas used during factory calibration of the apparatus. This flow self-test reading may be recorded along with the standard dataset which frequently includes atmospheric conditions. Readings below the calibration target value produce an "Error" and are also recorded. The flow self-test configuration may be checked and the test may be repeated when an "Error" occurs. Upon successfully passing the flow self-test, the operator may choose to exit the procedure and purge the apparatus 100 with air or continue on to the readily detectable test procedure.

The apparatus may be configured to maintain a number of data files in support of calibration, readings, periodic GNSS fix, self-test and/or errors. Individual folders may contain the respective files, for example purposes only, "Config" may contain configuration (e.g., calibration and/or instrument configuration) files, "R" may contain readings files, "F" may contain fix (e.g., periodic fixes) files, and/or "S" may contain system (e.g., self-test and/or error) files. It will be appreciated that the folders and files may be identified by any desired folder or file name.

In one embodiment, specific usage of each file type may be as follows. The configuration file may include calibration values and/or instrument configuration settings. Calibration values may include but are not limited to $k_{LCD}$, $k_{CAL}$, blower speed, calibration date, calibration time, and/or target value. Configuration values often include operational times for various functions. The recorded "dataset" in the readings file may include, but is not limited to, raw sensor data, corrected readings, $P_{actual}$, $T_{actual}$, actual longitude, actual latitude, UTC timestamp taken when the "read" key was pressed, and/or satellite information. The periodic fix file may include, but is not limited to, actual longitude, actual latitude, concurrent UTC timestamp, and/or satellite information. Self-test and error files may be contained in the system folder. Self-test files may include but are not limited to self-test status, uncorrected reading, actual longitude, actual latitude, concurrent UTC timestamp, satellite information, battery level, and/or blower speed. The error file, if any, can contain status information related to any operational aspect of the instrument including, but not limited to, battery level, power supplies, communications, GNSS module, memory, file system, real-time clock, sensors, Bluetooth module, USB, WiFi, blower speed, configuration, and/or keypad.

What is claimed is:

1. A method for obtaining independent measurements of odorant concentration in a target odorized gas and target odorized gas concentration in a gas-air mixture, the method comprising the steps of:
   providing the target odorized gas to a testing apparatus to conduct a test;
   mixing the target odorized gas with ambient air to form a gas-air mixture in the testing apparatus;
   moving the gas-air mixture to a location where the gas-air mixture is sniffed to detect odor;
   determining the odorized gas concentration in the gas-air mixture; and
   quantitatively measuring the odorant concentration in the target odorized gas by the testing apparatus independently of determining the odorized gas concentration in the gas-air mixture.

2. The method of claim 1, wherein the step of determining the odorized gas concentration in the gas-air mixture during a test comprises detecting the ambient air density at the time of the test and dynamically applying the ambient air density to derive an accurate measurement of the target odorized gas concentration in the gas-air mixture.

3. The method of claim 1, wherein the step of quantitatively measuring the odorant concentration in the target odorized gas comprises using an electro-chemical sensor.

4. The method of claim 1, wherein the step of quantitatively measuring the odorant concentration in the target odorized gas comprises using one of the group consisting of electro-chemical sensors, spectrophotometry, ultraviolet spectroscopy, ion-mobility spectrometry, flame ionization, gas chromatography, specific gravity, mass spectrometry and infrared sensing.

5. The method of claim 1, wherein the testing apparatus includes a fixed speed blower having a speed fixed during a factory calibration of the testing apparatus, and wherein the step of mixing the target odorized gas with ambient air comprises introducing ambient air into the testing apparatus via the fixed speed blower at the factory-calibrated fixed speed.

6. the method of claim 5, wherein the factory-calibrated fixed speed of the blower is based on the air density at the time of factory calibration.

7. A method for obtaining independent measurements of odorant concentration in a target odorized gas and target odorized gas concentration in a gas-air mixture with a testing apparatus, the testing apparatus including a fixed speed blower having a speed fixed during a factor calibration of the testing apparatus, the factory-calibrated fixed speed based on the air density at the time of factory calibration, the method comprising the steps of:
   providing the target odorized gas to a testing apparatus to conduct a text,
   quantitatively measuring the odorant concentration in the target odorized gas by the testing apparatus,
   mixing the target odorized gas with ambient air introduced into the testing apparatus via the fixed speed blower at the factory-calibrated fixed speed to form a gas-air mixture in the testing apparatus;
   moving the gas-air mixture to a location where the gas-air mixture is sniffed to detect odor; and
   determining the odorized gas concentration in the gas-air mixture during a test by:
      determining an initial concentration of the target odorized gas in the gas-air mixture upon detection of odor;
      detecting an ambient air density at the time of the test; and
      automatically applying a dynamic correction algorithm to the determined initial concentration to compensate for any differences between the calibration air density and the ambient air density at the time of the test.

8. The method of claim 7, wherein the step of detecting an ambient air density is determined using ambient temperature and pressure data.

9. The method of claim 7, wherein the step of detecting an ambient air density is determined using ambient temperature, pressure and humidity data.

10. The method of claim 7, further comprising the step of automatically recording the odorant concentration in the target odorized gas and the initial concentration and the corrected concentration of the target odorized gas in the gas-air mixture.

11. A method for accurately determining the relative gas concentration of a target odorized gas in a gas-air mixture in ambient atmospheric conditions using a testing apparatus previously calibrated at a calibration air density, the method comprising the steps of:
   determining an initial concentration of the target odorized gas in the gas-air mixture;
   determining an ambient air density when the initial concentration of the target odorized gas is measured; and calculating a corrected concentration based on a ratio of the calibrated air density and the ambient air density when the initial concentration of the target gas is measured.

12. The method of claim 11, wherein the step of detecting an ambient air density is determined using ambient temperature and pressure data.

13. The method of claim 11, wherein the step of detecting an ambient air density is determined using ambient temperature, pressure and humidity data.

14. The method of claim 11, further comprising the step of automatically recording the initial concentration and the corrected concentration of the target odorized gas in the gas-air mixture.

15. The method of claim 11, further comprising the steps of:
   providing the target odorized gas to the testing apparatus to conduct a test;
   mixing the target odorized gas with ambient air to form a gas-air mixture in the testing apparatus; and
   moving the gas-air mixture to a location where the gas-air mixture is sniffed to detect odor.

16. The method of claim 15, wherein the testing apparatus includes a fixed speed blower having a speed fixed during a factory calibration of the testing apparatus, and wherein the step of mixing the target odorized gas with ambient air comprises introducing ambient air into the testing apparatus via the fixed speed blower at the factory-calibrated fixed speed.

17. A method for accurately determining the relative gas concentration of a target odorized gas in a gas-air mixture in ambient atmospheric conditions using a testing apparatus previously calibrated at a calibration air density, the method comprising the steps of:
   mixing the target odorized gas with ambient air to form the gas-air mixture;
   moving the gas-air mixture to a location where the gas-air mixture is sniffed to detect odor;
   determining an initial concentration of the target odorized gas in the gas-air mixture upon detection of odor; and
   automatically applying a dynamic correction algorithm to the determined initial concentration to compensate for any differences between the calibration air density and an ambient air density at the time of the test.

18. The method of claim 17, further comprising the step of automatically recording the initial concentration, corrected concentration, time and date of the test, and geographical location at which the test is taken.

19. The method of claim 17, further comprising the step of determining an ambient air density when the initial concentration of the target odorized gas is determined.

20. The method of claim 19, wherein the step of determining an ambient air density is determined using ambient temperature and pressure data.

21. The method of claim 19, wherein the step of determining an ambient air density is determined using ambient temperature, pressure and humidity data.

* * * * *